(12) United States Patent
Laugere et al.

(10) Patent No.: US 9,731,073 B2
(45) Date of Patent: Aug. 15, 2017

(54) DISPENSE INTERFACE

(71) Applicant: Sanofi-Aventis Deutschland GmbH, Frankfurt am Main (DE)

(72) Inventors: Frederic Laugere, Bedfordshire (GB); Cristian Popa, Norfolk (GB); Ben Impey, Cambridgeshire (GB); Andrew MacLeod, Cambridgeshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 163 days.

(21) Appl. No.: 14/398,953

(22) PCT Filed: May 16, 2013

(86) PCT No.: PCT/EP2013/060161
§ 371 (c)(1),
(2) Date: Nov. 4, 2014

(87) PCT Pub. No.: WO2013/171310
PCT Pub. Date: Nov. 21, 2013

(65) Prior Publication Data
US 2015/0141928 A1    May 21, 2015

(30) Foreign Application Priority Data

May 16, 2012    (EP) .................................... 12168373

(51) Int. Cl.
*A61M 5/19* (2006.01)
*A61M 5/24* (2006.01)
(Continued)

(52) U.S. Cl.
CPC ............ *A61M 5/19* (2013.01); *A61M 5/2066* (2013.01); *A61M 5/2448* (2013.01);
(Continued)

(58) Field of Classification Search
CPC .. A61M 2039/1083; A61M 2039/1088; A61M 2207/00; A61M 39/10; A61M 5/19;
(Continued)

(56) References Cited

U.S. PATENT DOCUMENTS 3,604,410 A * 9/1971 Whitacre ........... A61B 5/15003
                                                    600/575
3,944,261 A * 3/1976 Reed ..................... A61M 39/10
                                                    156/73.1
(Continued)

FOREIGN PATENT DOCUMENTS

DE          10233925 A1    2/2004
WO      2011117404 A2    9/2011

*Primary Examiner* — Quynh-Nhu H Vu
(74) *Attorney, Agent, or Firm* — McDonnell Boehnen Hulbert & Berghoff LLP

(57) ABSTRACT

The invention relates to a dispense interface for an ejection device comprising a first part and a second part, at least a first opening, a second opening and a third opening, a fluidic channel and a connection element for each of the openings, wherein the first part is joined to the second part to form at least a part of the fluidic channel connecting the openings with each other and wherein at least one connection element is configured to accept a needle assembly for a fluid tight connection with the corresponding opening and wherein at least one connection element is configured to provide a releasable push fit connection for a fluid tight connection with an ejection device in order to reduce the complexity and provide an easy usage of the dispense interface and at the same time overcome the problems of material compatibility and cross contamination. The invention also relates to a system with a dispense interface according to the invention. The invention further relates to a method for preparing a dispense interface according to the invention.

13 Claims, 13 Drawing Sheets

(51) Int. Cl.
*A61M 5/28* (2006.01)
*A61M 5/20* (2006.01)
*A61M 39/10* (2006.01)

(52) U.S. Cl.
CPC ............. *A61M 5/284* (2013.01); *A61M 39/10* (2013.01); *A61M 2039/1083* (2013.01); *A61M 2039/1088* (2013.01); *A61M 2207/00* (2013.01); *Y10T 29/49945* (2015.01)

(58) Field of Classification Search
CPC .. A61M 5/2066; A61M 5/2448; A61M 5/284; Y10T 29/49945
See application file for complete search history.

(56) References Cited

U.S. PATENT DOCUMENTS

| | | | | |
|---|---|---|---|---|
| 4,979,942 A | * | 12/1990 | Wolf | A61B 17/00491 222/137 |
| 5,271,527 A | * | 12/1993 | Haber | A61M 5/19 222/137 |
| 5,478,323 A | | 12/1995 | Westwood et al. | |
| 5,505,704 A | * | 4/1996 | Pawelka | A61M 5/19 604/191 |
| 5,582,596 A | * | 12/1996 | Fukunaga | A61B 17/00491 222/137 |
| 2006/0089604 A1 | * | 4/2006 | Guerrero | A61M 5/1408 604/247 |
| 2008/0109002 A1 | * | 5/2008 | Delmotte | A61B 17/8816 606/93 |
| 2008/0167621 A1 | * | 7/2008 | Wagner | A61M 5/19 604/191 |
| 2011/0118659 A1 | * | 5/2011 | Maaskamp | A61M 5/19 604/28 |
| 2011/0118664 A1 | * | 5/2011 | Greter | A61B 17/00491 604/82 |
| 2012/0175384 A1 | * | 7/2012 | Greter | A61M 5/19 222/137 |
| 2013/0197447 A1 | * | 8/2013 | Smith | A61M 5/19 604/191 |

* cited by examiner

DISPENSE INTERFACE

CROSS REFERENCE TO RELATED APPLICATIONS

The present application is a U.S. National Phase Application pursuant to 35 U.S.C. §371 of International Application No. PCT/EP2013/060161 filed May 16, 2013, which claims priority to European Patent Application No. 12168373.4 filed May 16, 2012. The entire disclosure contents of these applications are herewith incorporated by reference into the present application.

FIELD OF INVENTION

The present patent application relates to an ejection device, for example a medical device, for delivering at least two liquids, such as liquid drug agents, from separate reservoirs. Such drug agents may comprise a first and a second medicament. The medical device includes a dose setting mechanism for delivering the drug agents automatically or manually by the user.

BACKGROUND

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

SUMMARY

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second integrated proximal needle. The first and second needles pierce a first reservoir containing a primary compound and a second reservoir containing a secondary compound, respectively.
2. Attach a dose dispenser, such as a double-ended needle assembly, to a distal end of the dispense interface. In this manner, a proximal end of the needle assembly is in fluidic communication with both the primary compound and secondary compound.
3. Dial up/set a desired dose of the primary compound from the injection device, for example, via a graphical user interface (GUI).
4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.
5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.
6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

The dispense interfaces in the state of the art are, however, often of complex design. In order to provide the manifold to lead the medicaments from two different reservoirs to a single outlet, multiple complex and/or small parts need to be produced and assembled. In particular, the first and second proximal needle which need to pierce the first and the second reservoir respectively need to be integrated in the manufacture process. A large part count and the corresponding complicated assembly steps can cause the dispense interface to be difficult to manufacture and expensive.

Additionally, the dispense interface is regularly kept at the drug delivery device for a longer period of time. That means that only the dose dispenser in form of a double ended needle, for instance, is exchanged for every or nearly every injection procedure. The dispense interface, however, remains at the drug delivery device. An exchange of the dispense interface itself is regularly only necessary, when the reservoirs of the drug delivery device need to be exchanged.

This causes requirements for the material and design of the dispense interface to be fulfilled. Since the drug agents from the first and/or the second reservoir remain inside the dispense interface after a dispense procedure, a material compatibility of the parts of the dispense interface being in contact with the drug agents needs to be provided. No harmful substances must diffuse into the drug agents, since these would then be delivered to the patient with the next delivery procedure. Hence a biocompatibility is required, which guarantees that either no or negligible amounts of substances can diffuse into drug agents or are set free into the liquid.

Furthermore, if the dispense interface remains attached to the drug delivery device the different drug agents also start to diffuse into each other over time. A cross-contamination of the drug agents from one reservoir into the other reservoir needs to be prevented for the above mentioned reasons of stability, compromised therapeutic performance and toxicology, for example.

In order to prevent such cross-contamination, valves that prevent backflow can be implemented in the dispense interface. This, however, increases the part count and thus the complexity and cost during the production of the dispense interface. Additionally, a septum is often provided at the outlet of the dispense interface, since the dispense interface needs to be sealed, when it is connected to the reservoirs but there is no dose dispenser attached.

In light of the aforementioned, the invention faces the technical problem of reducing the complexity and providing an easy usage of the dispense interface and at the same time overcoming the problems of material compatibility and cross contamination.

The technical problem is solved by a dispense interface for an ejection device comprising a first part and a second part, at least a first opening, a second opening and a third opening, a fluidic channel and a connection element for each of the openings, wherein the first part is joined to the second part to form at least a part of the fluidic channel connecting the openings with each other and wherein at least one connection element is configured to accept a needle assembly for a fluid tight connection with the corresponding opening and wherein at least one connection element is configured to provide a releasable push fit connection for a fluid tight connection with an ejection device.

By providing a dispense interface comprising a first and a second part being joined together to form at least part of the fluidic channel, the production and assembly of the dispense interface can be kept simple and cost efficient.

At the same time, by providing one connection element for each of the openings connected by the fluidic channel for either the connection with a needle assembly or with an ejection device, the production and assembly of the dispense interface is simplified, since the integration of the needles into the dispense interface during the manufacture of the dispense interface does not need to be taken care of. The needle assemblies are thus understood to be separate parts from the dispense interface.

Additionally, with the connection elements a convenient way for the user to attach a needle assembly to the dispense interface and to attach and detach the dispense interface to the ejection device is provided.

The cost efficient and easy production process allows the dispense interface to be replaced frequently, thus reducing the risk of contamination. In particular, it enables the dispense interface to be used as a single-use item. That means that after a single delivery procedure with an ejection of a liquid or a drug agent through dispense interface the dispense interface can be detached from the ejection device and discarded.

The ejection device can, for instance, be a medical device such as a drug delivery device.

During an ejection procedure, a liquid may enter the dispense interface through the first opening and another liquid may enter the dispense interface through the second opening. Therefore, these openings can be considered as inlets. Guided by the fluidic channel, the liquids can then leave the dispense interface via the third opening, which can be considered as an outlet. The dispense interface can thus be seen as a manifold.

The first and second connection elements corresponding to the first and second opening, respectively, are preferably configured to each provide a releasable push fit connection for a fluid tight connection with an ejection device. The first and second connection element may guide the liquids of the reservoirs of the ejection device to the first and second opening of the dispense interface. The needle assembly attached to the third connection element corresponding to the third opening can serve as a dose dispenser comprising an injection needle, for example.

It is preferred that the dispense interface comprises exactly three openings, wherein, as before, one opening serves as an outlet, which is in the following referred to as the third opening, and two openings serve as inlets, which are in the following referred to as the first and second openings. However, different numbers of inlets and outlets or different numbers of connection elements either configured to accept a needle assembly or configured to provide a push fit connection for a fluid tight connection with an ejection device can be provided.

The connection elements configured to accept a needle assembly can in particular be adapted for the connection of standard needle assemblies. A needle assembly is understood to be a needle with connection means for connecting the needle assembly to the connection elements. Such connection means of the needle assembly can comprise a hub, which can be threaded onto the connection elements for example. The needle assembly can also comprise a cylindrically shaped tapered hub for a friction fit connection. The connection element configured to accept a needle assembly need to be adapted to the corresponding needle assembly to be attached to the dispense interface.

The connection elements configured to provide a push fit connection for a fluid tight connection with an ejection device can be designed as hollow cylinders, for example, which are adapted to the cylinders provided with the ejection device and establishing a form fit or a friction fit with the ejection device.

It is preferred that the connection elements configured to provide a releasable push fit connection with an ejection device are designed identically, although it is also possible to provide different connection elements.

Since the dispense interface is only in connection with the reservoirs of the ejection device substantially during the ejection procedure, there is only a short time for possible substances or chemicals in the dispense interface to diffuse into the liquid ejected by the ejection device and guided through the fluidic channel.

There is also substantially no time for the liquids within the reservoirs to become cross-contaminated, since the dispense interface is directly detached after the ejection procedure as it can be thrown away.

Furthermore there is no need for a septum in the dispense interface, since an exchange of the needle assembly is not necessary, since after each injection an exchange of the whole dispense interface can take place. A new needle assembly can be attached to the corresponding connection element of a new dispense interface after or before attaching the dispense interface to the ejection device and establishing a fluid tight connection between the reservoirs and the dispense interface.

The channel or a part of the channel can be provided on a surface of the first part and/or the second part. By joining the first and the second part, the fluidic channel is then established. This can facilitate the provision of small fluidic channels in the dispense interface.

The joining of the first part and the second part can be realized by gluing or plastic welding. The latter can be realized by laser welding or ultrasonic welding for example. It is also possible to use joining techniques where the used or resulting substances do not show a long lasting biocompatibility, since the liquids are only in contact with the dispense interface for a short period of time.

It is also possible to join the first part and the second part by friction and/or positive fit. The connection needs to be tight and long lasting enough to provide leak tightness at least during a single ejection process.

Although the dispense interface may comprise more than two parts, it is preferred that the dispense interface comprises precisely a first and a second part. In this way, the complexity of the production and assembly of the dispense interface can be kept low.

As a consequence of the above mentioned, the complexity of the dispense interface is reduced, an easy usage of the dispense interface is provided and at the same time the problems of material compatibility and cross-contamination are overcome.

According to one embodiment of the dispense interface according to the invention at least one of the first part and the second part is produced by injection molding. With this manufacturing process at least one of the parts can be produced from plastic, such as a thermoplastic or a thermosetting material. It is preferred that both or all parts are produced from plastic. This reduces the operating expenses and costs of the manufacturing process of the dispense interface making it suitable for a low cost single-use component.

For instance, polymer materials may be used in injection moulding of the first and/or second part. Polymer materials are typically biocompatible. For instance, COP (cyclo-olefin polymer) materials may be used in injection moulding of the parts. COP materials have a high biocompatibility. For instance, COP materials have little to no extractables and most COP material can undergo sterilization by gamma radiation, steam and/or ethylene oxide.

Potential problems of material compatibility, absorption and contamination between the fluids (e.g. drugs) and the polymer material are thus overcome independently of the time of contact between dispense interface and liquid.

The first and/or second part can in particularly be molded including the connection elements as integral parts of either the first or the second part. The connection elements are likewise preferably produced from a plastic material and are an integral component with the first or second part. This reduces the complexity and costs of the manufacture and thus of the dispense interface itself.

This production method is particularly advantageous in combination with the first part and the second part forming the fluidic channel connecting the openings with each other. Since it is difficult to provide small fluidic channels within components by means of injection molding, the channel or a part of the channel only needs to be provided on a surface of the first part and/or the second part, for example by a modification in form of a recess. By joining the first and the second part, the fluidic channel is established.

When the first part comprises the third opening and the third connection element and when the second part comprises the first opening with the first connection element and the second opening with the second connection element, an advantageous geometric distribution of the openings and the corresponding connection elements can be provided. Furthermore, the first and second openings and connection elements can be provided into one direction on the second part and the third opening and connection element can be provided in another direction. This simplifies the usage of the dispense interface for the user. It is in particular preferred, when the first and second connection elements have a parallel orientation, while the third connection element has an antiparallel orientation with respect to the first and second connection element.

A preferred design of the dispense interface can be achieved, when the first part and the second part have an elongateshape. In this way, a compact design adapted to the fluidic channel is achieved resulting in low cost for the dispense interface, such that the cost and the size of a single-use component can be reduced. The first part and the second part have preferably a substantially plate like design. That means that the parts are substantially constantly thin in a direction perpendicular to the elongate direction. In the same direction perpendicular to the elongate direction the connection elements can protrude from the first and/or second part.

When the first opening is located at a first end of the second part and the second opening is located at a second end of the second part, a compact dispense interface can be provided. Preferably, the first and second openings are spaced apart by the distance of the reservoirs.

It is further advantageous, when the third opening is located between the first end and the second end of the first part. The third opening can in particular be provided substantially in the middle of the first part. This is advantageous in combination with the first opening being located at the first end of the second part and the second opening being located at the second end of the second part. A symmetric design can be achieved in this way resulting in similar or identical lengths of the fluid pathway from the first and the second opening to the third opening in each case. Due to the symmetrical design, the orientation of the dispense interface when attaching it to an ejection device does not need to be cared about. That means it does not make a difference, which of the first and second opening is connected to which reservoir. This increases the ease of use of the dispense interface.

When the at least one connection element configured to accept a needle assembly is configured for a releasable connection with a corresponding needle assembly, the needle assembly can be removed before the dispense interface is discarded. Furthermore, this design increases the compatibility with standard needle assemblies, since the needle assemblies according to industrial standard are chiefly provided with releasable connection means, such as a hub.

According to another embodiment of the dispense interface according to the invention, the fluidic channel comprises a substantially linear passage with a passage branching off for each opening. Due to a straight, linear connection between the branching-off passages leading to the openings, a short fluidic channel can be provided. This results in a low waste of drug agents, which remain in the fluidic channels after an ejection procedure. The substantially linear passage is preferably oriented in the elongated direction of the dispense interface, while the branching-off passages are preferably oriented perpendicular to the substantial linear passage of the fluidic channel.

An easy and quick to use the dispense interface can be provided, when at least one of the connection elements is configured for at least one of a friction fit and a positive fit. This can be a friction and/or positive fit with a needle assembly and alternatively or additionally a friction and/or positive fit with an ejection device. The needle assembly or the ejection device can then be quickly and easily connected to the corresponding connection element, while at the same time a fluid tight connection can be provided. Preferably, all connection elements are configured for at least one of a friction fit and a positive fit with either a needle assembly or an ejection device.

A safe and at the same time easy connection can in particular be provided, when the at least one connection element configured to accept a needle assembly provides the male part of a Luer fitting. Basically, there are two designs of Luer taper connections, a so called Luer-Lok and a so called Luer-Slip. Luer-Lok fittings are securely joined by means of a tabbed hub on the female fitting which screws into threads in a sleeve on the male fitting of the needle assembly. Luer-Slip fittings conform to Luer taper dimensions and are pressed together and held by friction. It is also possible to provide an additional positive fit for Luer-Slip fittings. Such a design of at least one connection element guarantees a high compatibility with needle assemblies available on the market, increasing the ease of use of the dispense interface, since the user generally knows the working principle of a Luer fitting.

It is also possible that the connection elements provided for a releasable push fit connection with an ejection device or even all connection elements provide the male part of a Luer fitting.

When the fluidic channel is configured such that a liquid can flow freely from any region of higher pressure to any region of lower pressure, the dispense interface is particularly easy and cost efficient to manufacture. No components, in particular valves, are provided in the fluidic channel, which would increase the efforts and expenses during the manufacture of the dispense interface. The risk of a cross-contamination or a diffusion of substances into the liquid guided with the dispense interface is counteracted by the fact that the dispense interface can be produced so efficiently and cost-effectively, that the dispense interface can be used as a single-use item. Hence, there is only a short period of time, in which the guided liquid and the dispense interface are in contact reducing the risk of any contaminations of the dispense interface.

Alternatively, it is also possible, that the fluidic channel comprises at least one non-return valve. This prevents or minimizes the back flow of a fluid back into one of the reservoirs. Additionally, the common volume can be reduced, in which both fluids from the reservoirs mix. This is advantageous, in case the user forgets to remove the dispense interface from the ejection device. In that case a cross-contamination can still be prevented. Especially, when the fluids are ejected one after another, the risk of a cross-contamination is higher, since there is a reduced counter pressure for the fluid from the one reservoir to enter the other reservoir compared to when both fluids are ejected simultaneously. Preferably, either a valve, such as a diaphragm valve, for each the first and the second opening is provided or a valve, such as a shuttle valve, which prevents backflow in both the first and the second opening is provided. In case more than two inlets are provided, a corresponding number of valves is preferably provided.

The at least one valve can either be an integral part of the dispense interface, for example by over molding the valve to the first and/or the second part. Alternatively the at least one valve can also be designed as a separate part and then assembled with first and second part during the manufacture. Possible valves are for example a diaphragm or flap valve, a shuttle valve, a (molded) duckbill valve, a flat spring, or rotation flap valve.

The technical problem is further solved by a system comprising a dispense interface according to the invention, at least one needle assembly and an ejection device. Preferably, there is provided one needle assembly for one connection element configured to accept a needle assembly.

The user can attach the needle assemblies to the connection elements of the dispense interface directly before an ejection procedure. For this, the connection element and the corresponding needle assembly are adapted to each other. Before or after the attachment of the needle assembly to the dispense interface, the user can attach the dispense interface to the ejection device, which has connection elements adapted for the connection elements of the dispense interface configured to provide a releasable push fit connection with the ejection device. The manufacture of the dispense interface is simplified, since an integration of needles in the dispense interface does not need to be provided during the manufacture of the dispense interface. Hence, the dispense interface can be exchanged more frequently, or even after every use.

To reduce the amount of cross-contamination, valves can be provided in the ejection device. In particular a valve can be provided for each connection element of the ejection device positioned between the reservoir and the dispense interface. The valve can also be an integral part of the reservoir.

As a consequence, the complexity of the dispense interface is reduced, an easy usage of the dispense interface is provided and at the same time the problems of material compatibility and cross contamination are overcome.

The technical problem is further solved by a method for preparing a dispense interface according to the invention comprising the steps of attaching the dispense interface by means of the push fit connection to an ejection device having at least two reservoirs such that a fluid tight connection is established between the at least two reservoirs and the dispense interface, and attaching a needle assembly to the at least one connection element configured to accept a needle assembly of the dispense interface. The two steps can be conducted in either temporal order, however it is preferred that the dispense interface is attached to the ejection device before a needle assembly is attached to the dispense interface.

By attaching the dispense interface to the ejection device and attaching a needle assembly, preferably one needle assembly, to the corresponding connection elements of the dispense interface, it is possible to provide a dispense interface, the production of which is simplified, since an integration of the needles in the dispense interface does not need to be provided during the manufacture of the dispense interface. That means that the at least one needle assembly is not integrated into the dispense interface, but attached afterward the production of the dispense interface. The at least one needle assembly may be attached to the dispense interface already at the site of the manufacturer. Preferably, the user attaches the at least one needle assembly to the dispense interface after having taken the dispense interface out of a package and having attached the dispense interface to the ejection device. It is in particular possible and still economical for the user, to exchange the dispense interface more frequently, or even after every use.

Since the at least one needle assembly is separated from the dispense interface and attached after the production, for example manually by the user, and since at least one connection elements for a releasable push fit connection is provided, the complexity of the dispense interface is reduced and an easy usage of the dispense interface is provided. At the same time the problems of material compatibility and cross contamination are overcome, since the user establishes the connection of the dispense interface with the reservoirs directly before an ejection and the user can remove it directly afterwards as well.

When the user attaches the dispense interface to the ejection device, preferably the first connection element provides a fluid tight connection to the first reservoir of the ejection device, while the second connection element provides a fluid tight connection to the second reservoir of the ejection device.

The dispense interface may be secured in an engaged position with the ejection device. This can be done by fixing elements provided by the ejection device, for example. Such fixing elements, hooks or protrusions adapted to the dispense interface for instance, may establish a positive fit between the dispense interface and the ejection device. Alternatively, it is also possible that the dispense interface is fixed in the engaged position with the ejection device only by friction fit of the at least one connection element for the releasable push fit connection with the ejection device.

In case the needle tip of the at least one needle assembly is covered with a needle cover, the user needs to remove this cover before performing an ejection procedure.

Preferably, the method according to the invention further comprises the steps of ejecting a fluid from at least one of the reservoirs through the dispense interface and then removing the dispense interface form the ejection device.

These steps are performed after having attached the dispense interface to the injection device. When the dispense interface is removed after an ejection procedure, for example by the user, the risk of possible contaminations of the fluids and/or the reservoirs is reduced. Preferably, the dispense interface is removed directly after an ejection procedure. The dispense interface can then be discarded with or without the at least one needle assembly.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which.

DETAILED DESCRIPTION

Figure 1:
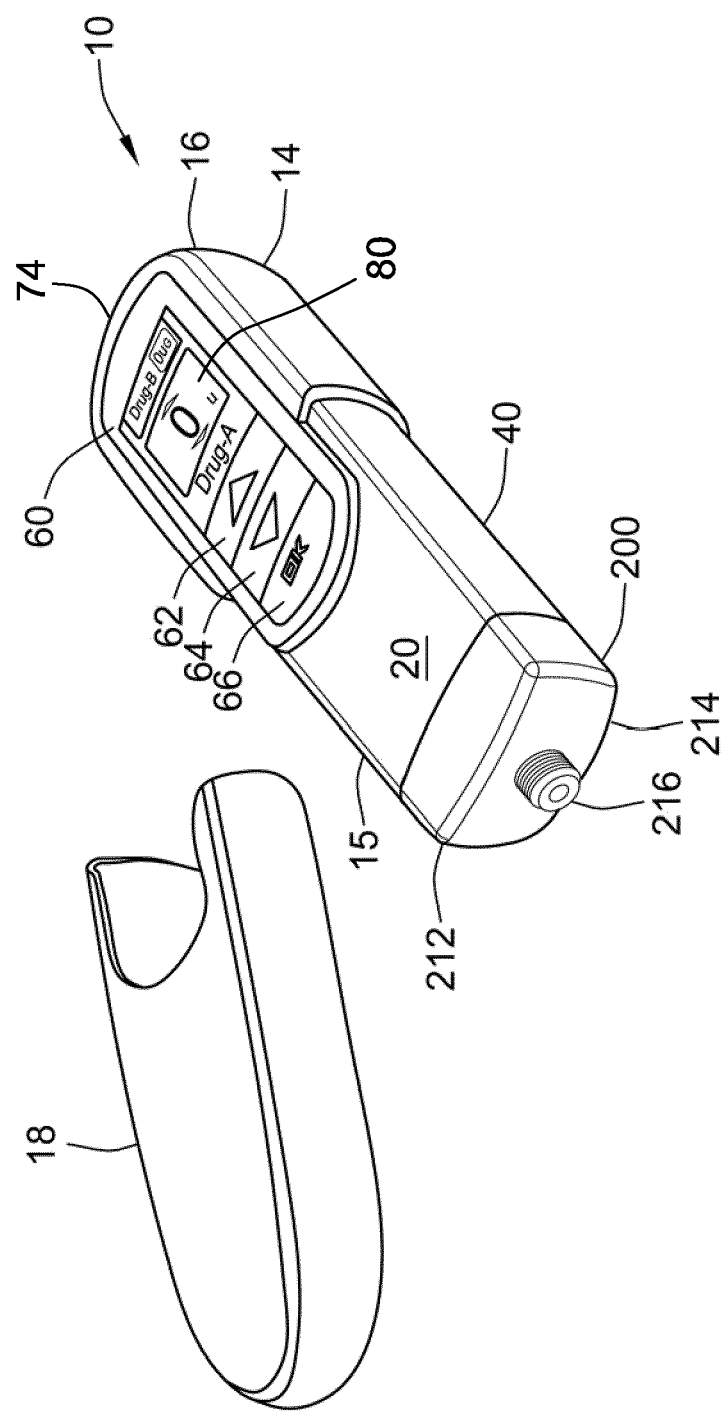
FIG. 1 illustrates a perspective view of a delivery device with an end cap of the device removed.
Figure 2:
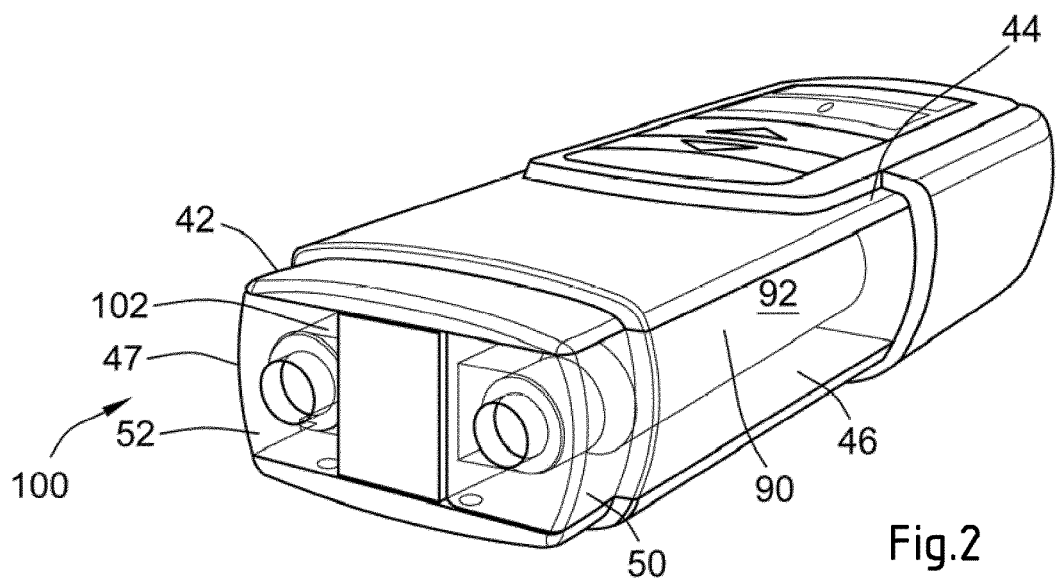
FIG. 2 illustrates a perspective view of the delivery device distal end showing the cartridge.

The ejection device in the form of a drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1). The user interface of the drug delivery device may comprise additional buttons, such as a "menu" button, a "back" button, or a "light" button to switch on an illumination of the display.

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 210 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
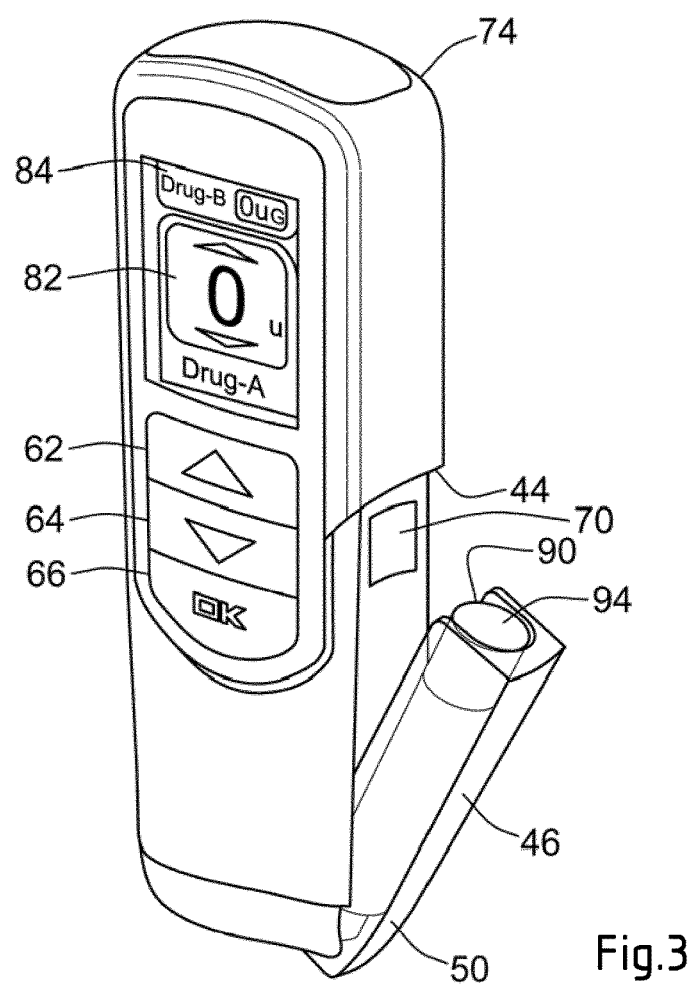
FIG. 3 illustrates a perspective view of the delivery device illustrated in FIG. 1 or 2 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
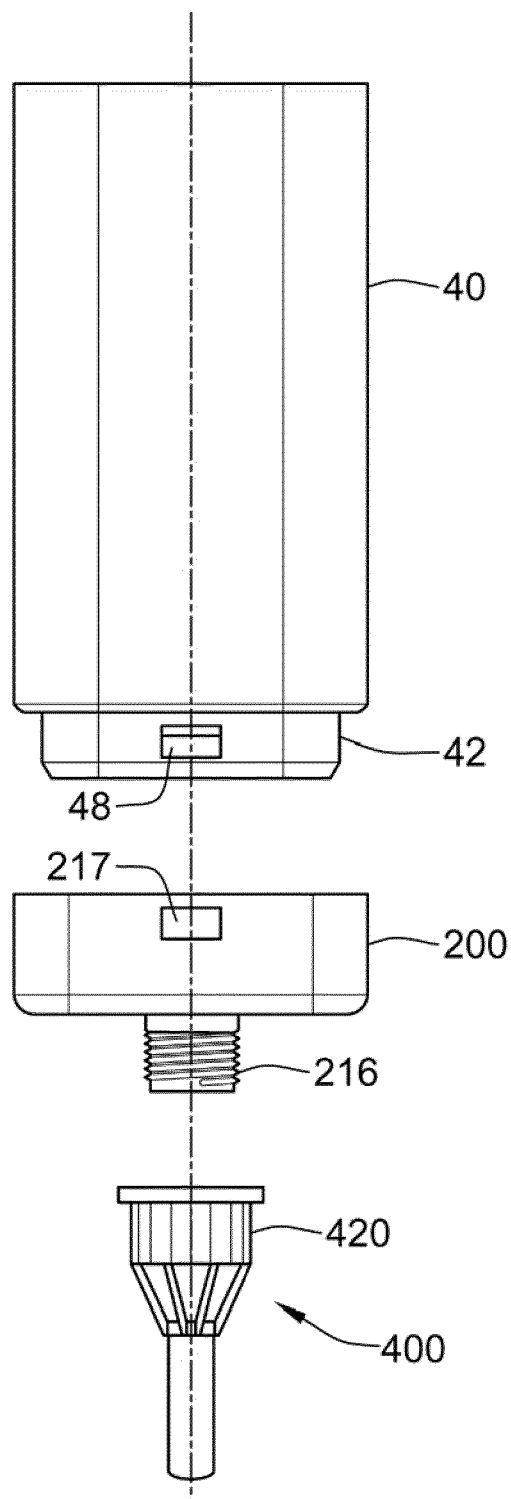
FIG. 4 illustrates a dispense interface and a dose dispenser that may be removably mounted on a distal end of the delivery device illustrated in FIG. 1.

As mentioned above when discussing FIG. 1, a dispense interface 200 can be coupled to the distal end of the cartridge holder 40. FIG. 4 illustrates a flat view of the dispense interface 200 unconnected to the distal end of the cartridge holder 40. A dose dispenser or needle assembly 400 that may be used with the interface 200 is also illustrated and is provided in a protective outer cap 420.

Figure 5:
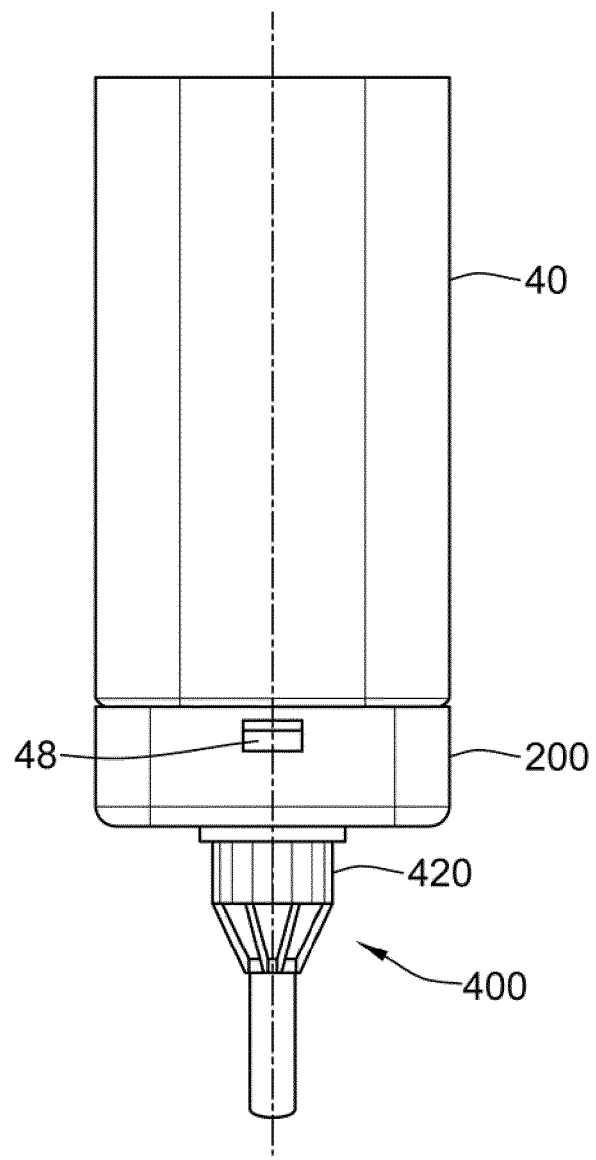
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means 48 between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
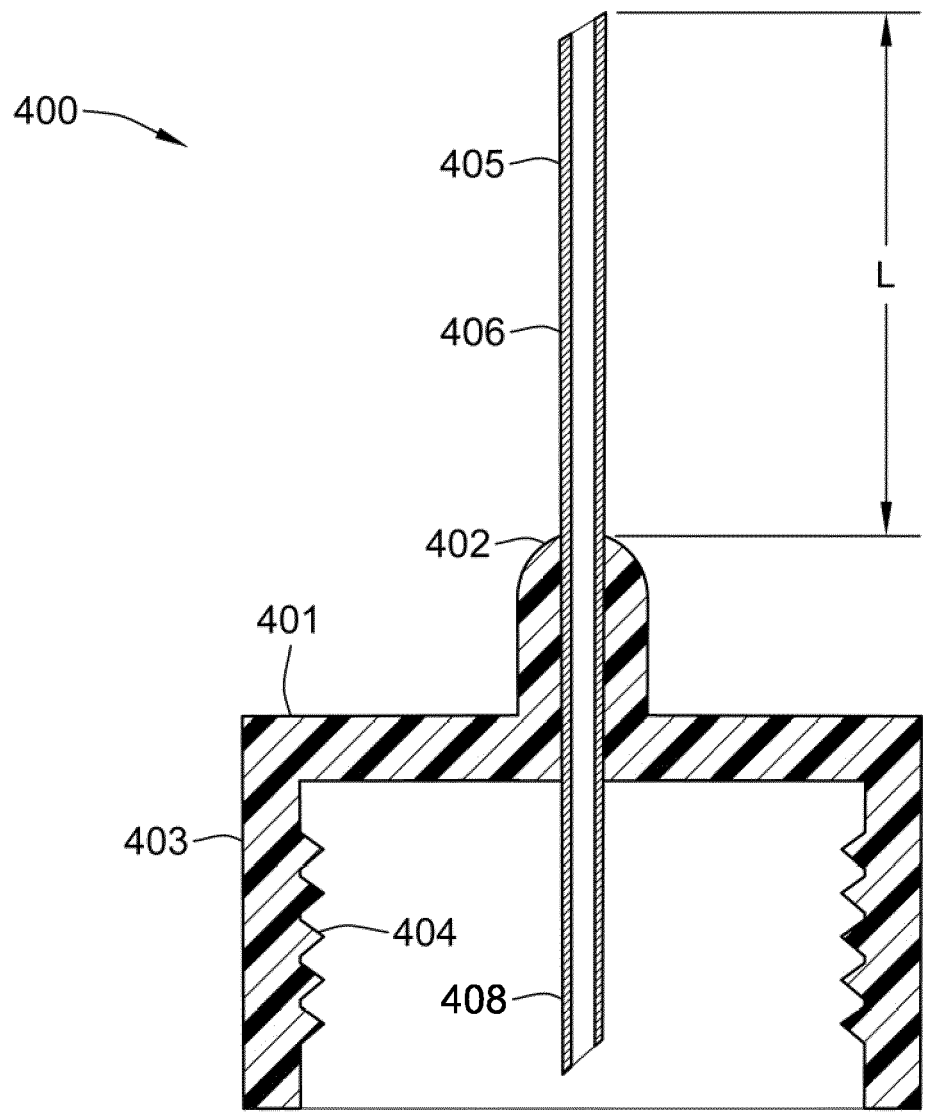
FIG. 6 illustrates one arrangement of a needle assembly that may be mounted on a distal end of the delivery device.
Figure 7:
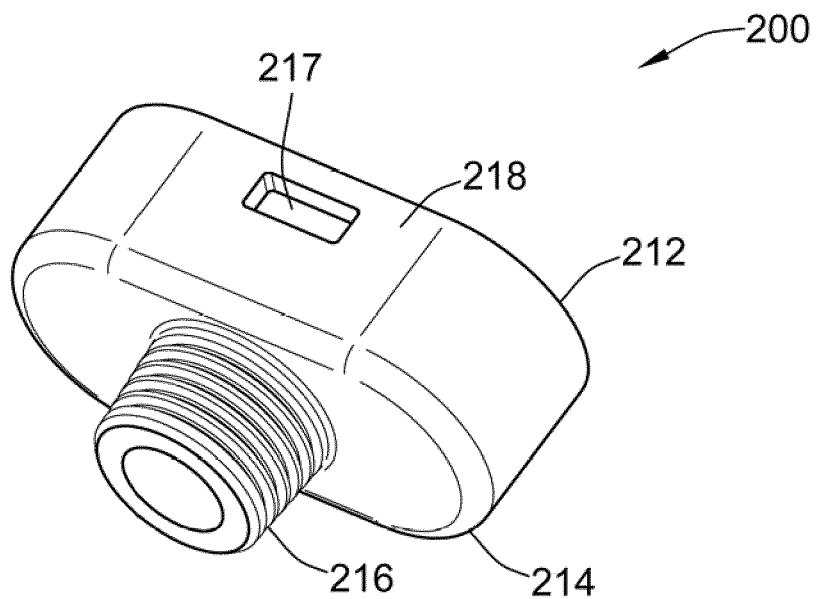
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 400 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 408 of the needle assembly 400 protrudes from an opposite side of the circular disc so that it is concentrically surrounded by the sleeve 403. In one needle assembly arrangement, the second or proximal piercing end 408 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:
 a. a main outer body 210,
 b. an first inner body 220,
 c. a second inner body 230,
 d. a first piercing needle 240,
 e. a second piercing needle 250,
 f. a valve seal 260, and
 g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
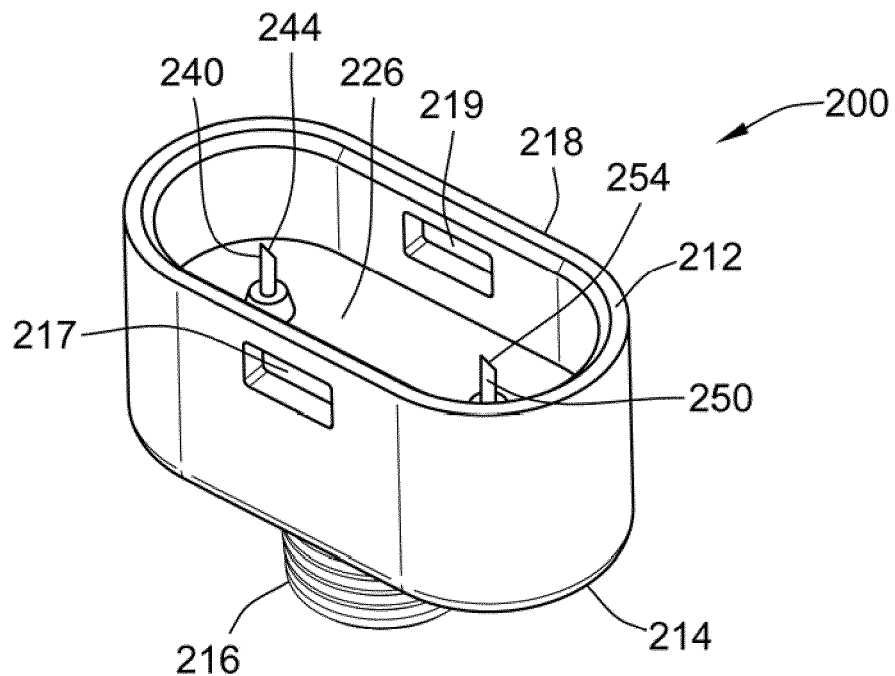
FIG. 8 illustrates another perspective view of the dispense interface illustrated in FIG. 4.
Figure 9:
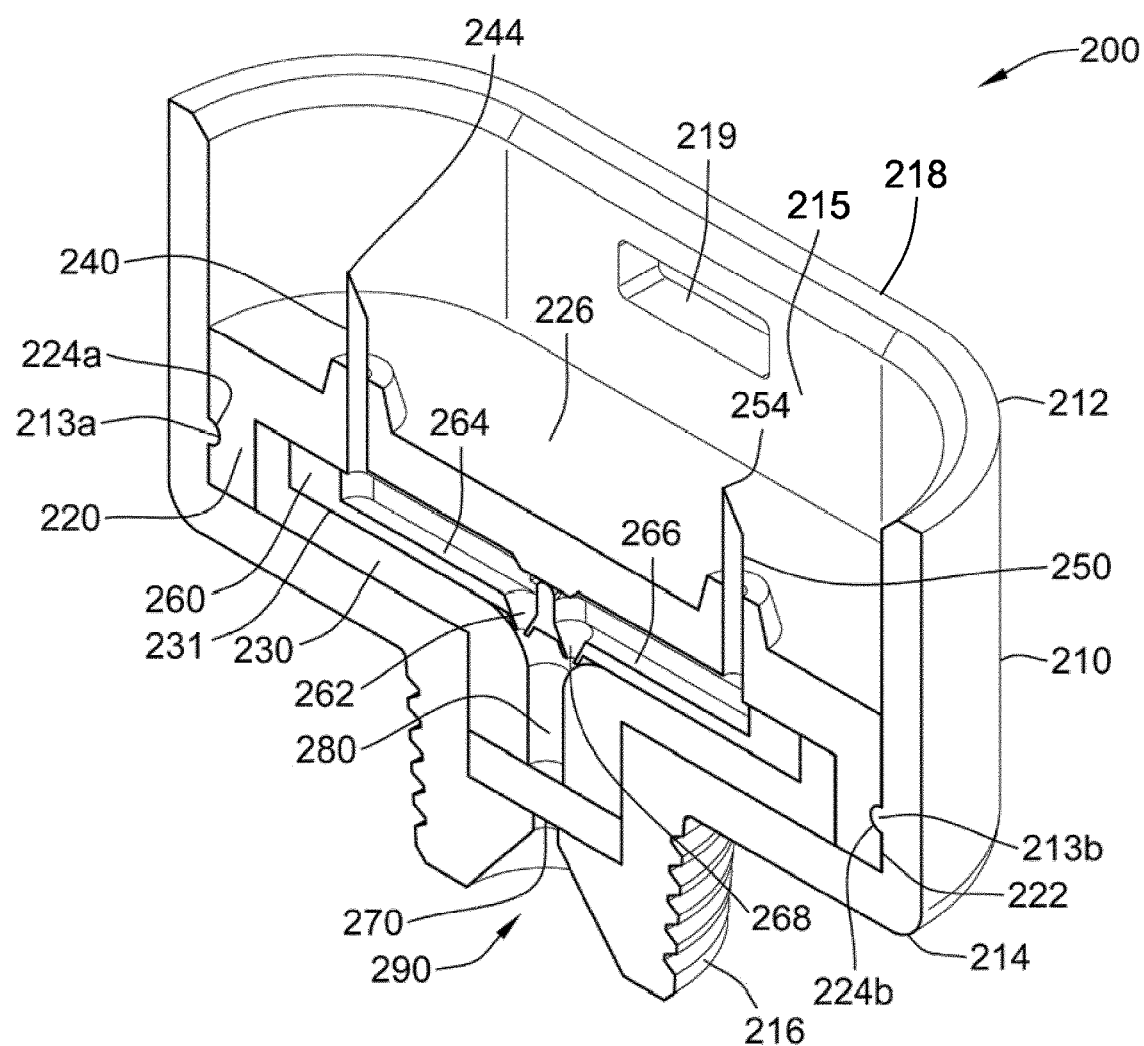
FIG. 9 illustrates a cross-sectional view of the dispense interface illustrated in FIG. 4.
Figure 10:
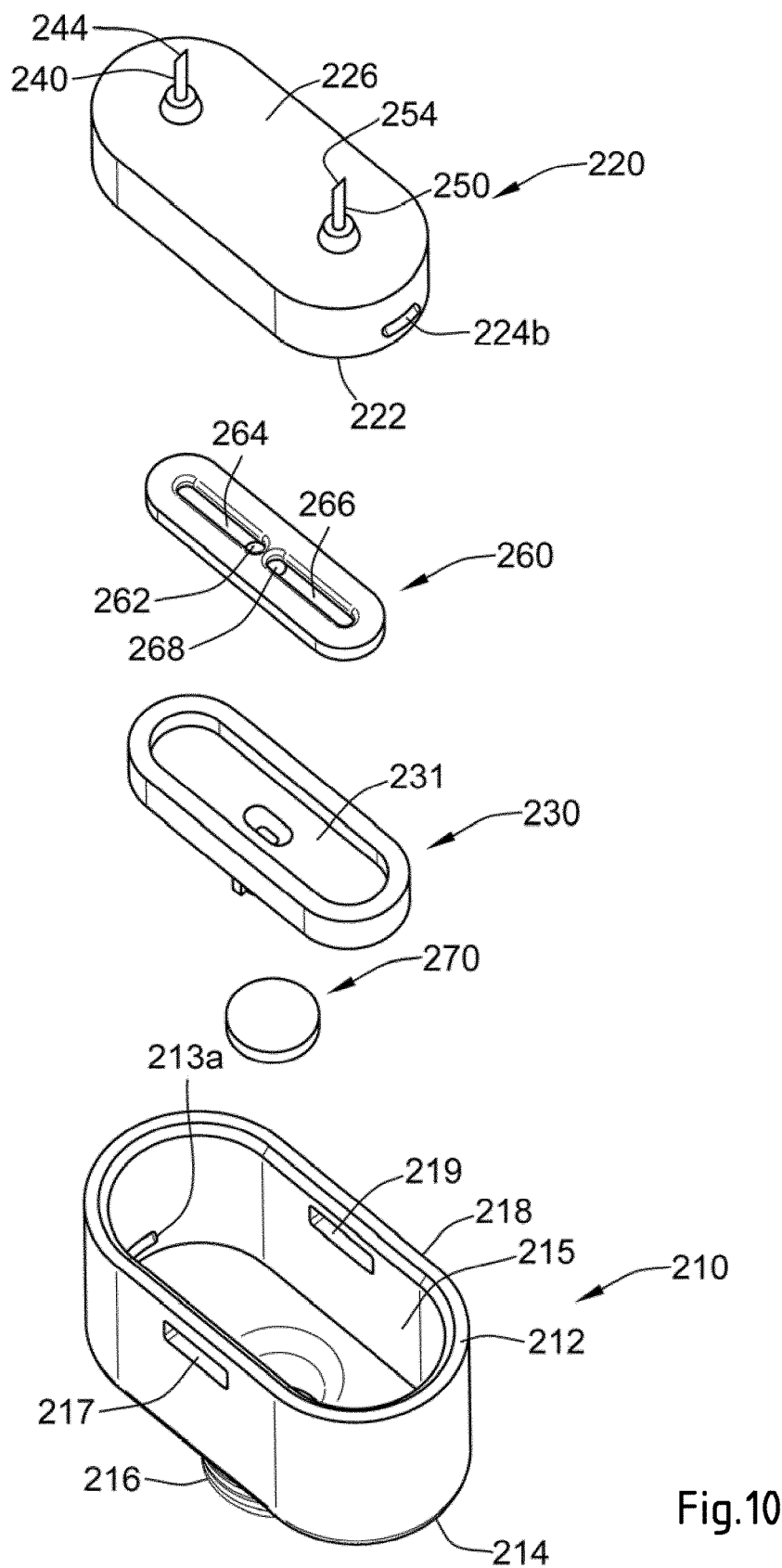
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
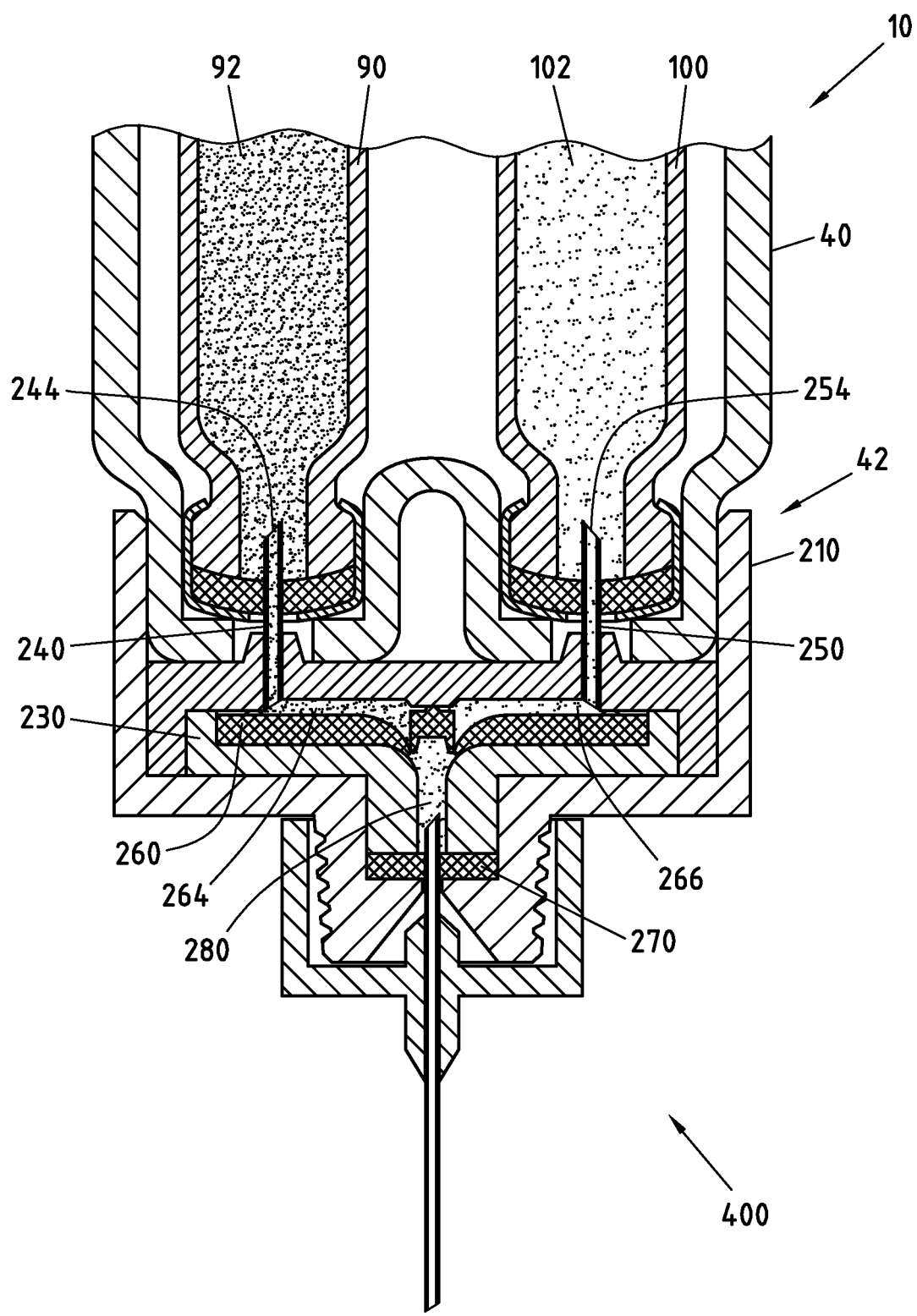
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Figure 12:
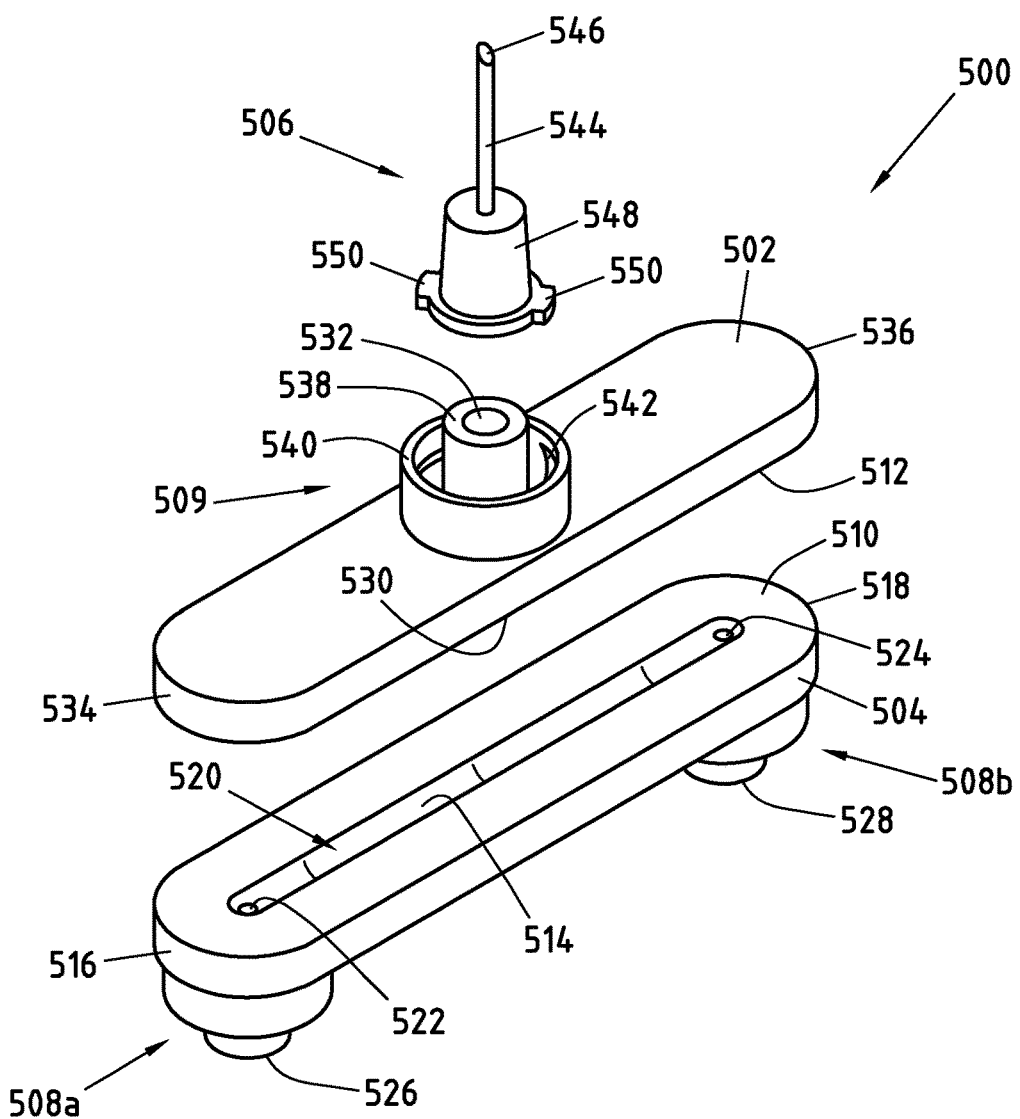
FIG. 12 illustrates a perspective view of a dispense interface according to the invention with the first part and the second part not joined and with one needle assembly not attached to the connection element.

FIG. 12 illustrates a perspective view of a dispense interface 500 according to the invention with the first part 502 and the second part 504 not joined to each other and with a needle assembly 506 not attached to the connection element 509 configured to accept the needle assembly 506. The dispense interface 500 further comprises the two connection elements 508a and 508b configured to provide a releasable push fit connection for a fluid tight connection with an ejection device (cf. FIG. 13).

The dispense interface 500 comprising the two parts 502 and 504 is not completely assembled yet. The two parts 502 and 504 are made of plastic and are produced by injection molding. The connection elements 509, 508a and 508b are produced together with the first part 502 and the second part 504, respectively, in the injection molding process. Both the first part 502 and the second part 504 are substantially plate-like and have an elongated shape. Only the connection elements 508a, 508b and 509 protrude from the plate-like shape of the first part 502 and the second part 504, respectively.

Figure 13:
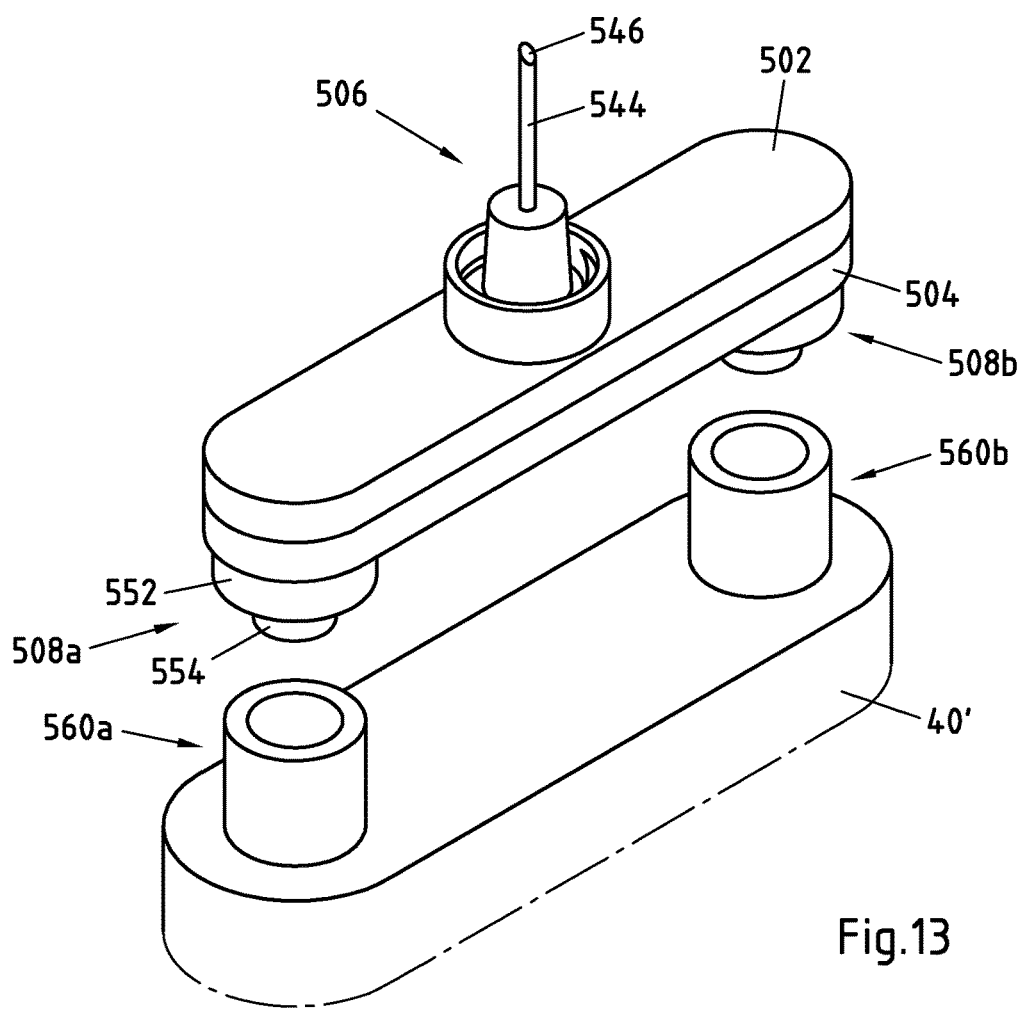
FIG. 13 illustrates the dispense interface of FIG. 12 with the first part joined to the second part, with the needle assembly attached and with an ejection device

The first part 502 and the second part 504 each comprise a substantially flat surface 510 and 512, respectively. The surface 510 of the second part 504 comprises a substantially linear recess 514 extending from the first end 516 to the second end 518 of the second part 504. When the first part 502 and the second part 504 are joined together (as shown in FIG. 13), the surface of the first part 502 in connection with the surface of the second part 504 form a substantial part of the fluidic channel 520. The first part 502 may comprise a similar recess to the recess 514 provided in the second part 504. The first part 502 may also be provided without a recess in the substantially flat surface 512. The cross section of the fluidic channel 520 may thus be circular or in the shape of a semi circle. It is also possible to provide other geometric shapes for the cross section of the fluidic channel 520, such as a rectangular or oval shape.

The fluidic channel 520 comprises two passages 522 and 524 branching-off substantially perpendicularly from the recess 514 in the second part 504. The passage 522 is located close to the first end 516 of the second part 504 and the passage 524 is provided close to the second end of the second part 504. The passages 522 and 524 provide the first opening 526 and the second opening 528 respectively. The opening 526 and 528 are covered by the corresponding first connection element 508a and second connection element 508b, both providing a releasable push fit connection for the connection with an ejection device.

The first part 502 also comprises a passage 530 on the surface 512. This passage 530 also branches off substantially perpendicularly from the fluidic channel 520 in the joined state of the first part 502 and second part 504. The passage 530 provides the third opening 532 of the fluidic channel 520. The passage 530 is located substantially in the middle of the first part 502, half way from each the first end 534 and the second end 536 of the first part 502. This way a similar or identical fluidic pathway is provided between the first opening 526 and the third opening 532 compared to the fluidic pathway between the second opening 528 and the third opening 532.

The connection element 509 comprises a first hollow cylinder 538 and a second hollow cylinder 540. The first hollow cylinder 538 surrounds the third opening 532 and is the male part of a Luer-Lok. The second cylinder 540 comprises an internal thread 542 for providing a positive fit with the needle assembly 506 to provide a Luer-Lok.

The needle assembly 506 comprises a needle 544 having a first end 546 and a second end, which second end is covered by a connection element in form of a needle hub 548. The needle hub 548 is designed as a tapered cylinder and provides the female part of a Luer fitting, in this case of a Luer-Lok. For this, the needle hub 548 comprises to projections 550 which can interact with the thread 542 of the second cylinder 540 of the third connection element 509. The tapered needle hub 548 interacts with the first cylinder 538 of the third opening 532 to provide a fluid tight connection between the third connection element 509 and the needle assembly 506.

FIG. 13 illustrates the dispense interface 500 of FIG. 12 with the first part 502 joined to the second part 504 and with the needle assemblies 506 attached. The first part 502 and the second part 504 can be joined by gluing or welding for example.

As illustrated in FIG. 13, the two connection elements 508 are configured to provide a releasable push fit connection for a fluid tight connection with the ejection device in form of a cartridge holder 40', which cartridge holder can be similar to the cartridge holder 40, for example. This yields a device, similar to the device 10. The connection elements 508 are designed identically in this exemplary embodiment. Thus, only the connection element 508a is described here, being representative for the two connection elements 508a and 508b. However, it is also possible to provide connection elements differing from each other.

The connection element 508a is in this example designed similar to the connection element 509 with the exception that there is no thread such as internal thread 542 provided, since the connection elements 508 are in this case push fit connectors. The connection elements 508 can provide a connection by friction fit with the corresponding connection elements of the ejection device. Here, two coaxially arranged cylinders 552, 554 are provided for the connection element 508a. These can be similar to the cylinders 538, 540 of the third connection element 509. The cylinders 552, 554 are adapted to the connection element 560a of the holder 40' to provide a releasable push fit connection.

The user can be provided with the dispense interface 500 as shown in FIG. 13, but without the needle assembly 506 attached to the dispense interface 500. The user would then take the dispense interface 500 out of the package and attach the needle assembly 506 to the dispense interface 500 to obtain a system of dispense interface 500, needle assembly 506 and cartridge holder 40' as shown in FIG. 13. The user could also attach the dispense interface 500 to the holder 40' first and then attach the needle assembly 506. It is possible that the needle assembly 506 is provided with covers for protecting the first end 546 of the needle 544.

In the state of the dispense interface 500 shown in FIG. 13, the user can attach the dispense interface to the ejection device 40', similar to the cartridge holder 40 of the ejection device 10. The dispense interface 500 with the needle assembly 506 then substitute the dispense interface 200 with the dose dispenser 400 (cf. FIGS. 1-11).

Figure 14:
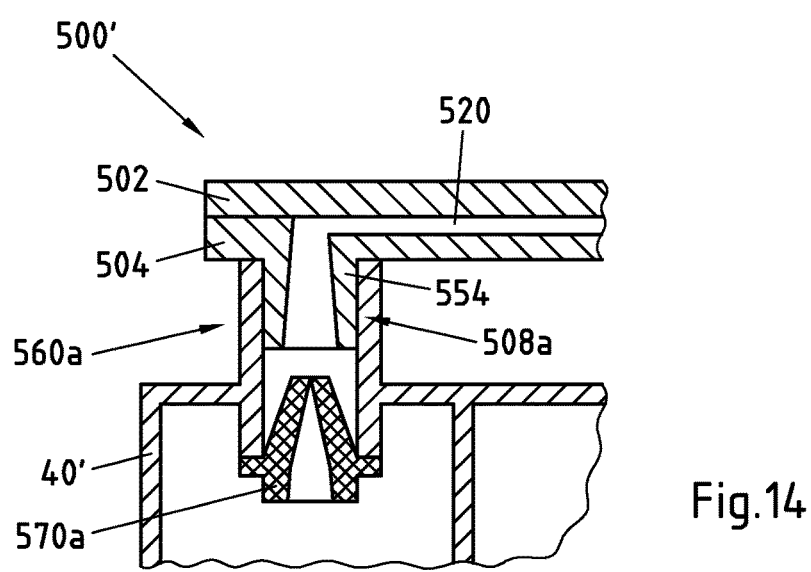
FIG. 14 illustrates a cross sectional view of second exemplary embodiment of a dispense interface and the ejection device of FIG. 13 in an attached state.

FIG. 14 illustrates a cross sectional view of second exemplary embodiment of a dispense interface 500 and the ejection device of FIG. 13 in an attached state. The dispense interface 500' only differs from the dispense interface 500 in that the connection elements 508 are designed as single cylinders (such as cylinders 554) providing a releasable push fit connection with the cartridge holder 40'.

The cartridge holder 40' also comprises one-way valves 570 for each of the connection elements 560 of the cartridge holder 40' (only valve 570a shown in FIG. 14). Theses valves 570 prevent a backflow of the medicaments 92, 102 into the reservoirs 90, 100 (cf. FIG. 11). The valve 570a is provided as a moulded duckbill valve. However, other types of non-return valves can be provided as well. The valves 570 can also be part of the cartridges 90, 100, for example.

The releasable push fit connection established by the connection elements 508 and 560 provide the fluid tight connection for the first and the second reservoirs 90, 100 (cf. FIG. 11). This establishes a fluid tight connection between the primary medicament 92 from the first reservoir with the outlet opening 532 of the fluidic channel 520 of the dispenser interface 500 or 500'. Simultaneously, this establishes a fluid tight connection between the secondary medicament 102 from the second reservoir with the outlet opening 532 of the fluidic channel 520 of the dispenser interface 500 or 500'.

The user can then start an ejection procedure with the device 10. The needle assembly 506 with the first end 546 of the needle 544 works as an injection needle. After the ejection of the fluids, the user can detach the dispense interface 500, 500' from the cartridge holder 40'. Since the dispense assembly can be used as a single-use item due to the efficient and simple production, the user can then discard the dispense interface 500, 500'.

Although, the dispense interface 500, 500' substitutes the dispense interface 200, features of the dispense interface 200 can also be combined with the exemplary embodiment 500, 500' of the dispense interface according to the invention. The dispense interface 500, 500' can for example be provided with a wall similar to wall 218 providing recesses 217, 219 in order to attachment the dispense interface 500 more securely to the cartridge holder 40, for example. Instead of the needle assembly 506, the needle assembly 400 with the corresponding connection elements in the form of the needle hub 216 can be provided, as well, for instance.

It is also possible to provide a dispense interface with more than three connection elements to provide the ejection of more than two fluids via a single outlet. It is further possible to provide the non-return valves in the dispense interface 500 such as the non-return valves 262, 268.

FIGS. 15a to 15e illustrate different embodiments of valve arrangements for a dispense interface 200 or 500. The exemplary valve arrangements can be provided alternatively to the valve seal 260 of dispense interface 200, for example, or they can be provided in the fluidic channel 520 of the dispense interface 500 similar to the design of dispense interface 200. In FIGS. 15a to 15e the same reference signs are used for parts which may be similar.

The valve arrangements may for instance be integrally formed with another part of the dispense interface, such as the first part 502 or the second part 504. Alternatively, the valve arrangement may for instance be manufactured separately from the other parts of dispense interface.

For instance, the valve arrangement may be inserted (e.g. potted/over-molded) into the first part 502 and/or the second part 504. For instance, the valve arrangement may at least partially be inserted (e.g. potted/over-molded) when the first part 502 and/or the second part 504 are injection molded. For instance, the valve arrangement may at least partially be inserted (e.g. mounted) in a separate step after the first part 502 and/or the second part 504 have been injection molded.

Figure 15A:
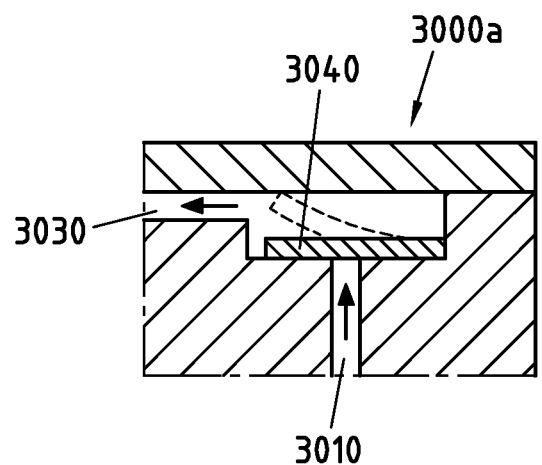
FIG. 15 illustrates different embodiments of valve arrangements, which can be used in a dispense interface according to the invention.

FIG. 15a illustrates a diaphragm/flap valve arrangement 3000a. The diaphragm/flap valve arrangement 3000a has an inlet 3010 and an outlet 3030. The inlet 3010 may for instance reside in fluid communication with one of the piercing needles 240, 250 of dispense interface 200 or openings 526, 528 of dispense interface 500, respectively, while the outlet 3030 may for instance reside in fluid communication with holding chamber 280 of dispense interface 200 or injection needle 544 of dispense interface 500. If a valve is already provided in the cartridge housing 40' of the ejection device, there is no necessity for additional valves in the dispense interface to prevent a backflow to the reservoirs 90, 100. However, it is possible to provide valve arrangements in the dispense interface 500 in any case.

The diaphragm/flap valve arrangement 3000a has flexible diaphragm/flap 3040. When the fluidic pressure in the inlet 3010 is increased (e.g. during a dose priming or a dose injecting step), the diaphragm/flap 3040 will change from an un-stressed state to a stressed state. In the stressed state, the fluidic pressure bends the diaphragm/flap 3040 as indicated by the arrow in FIG. 15*a* so that the diaphragm/flap valve arrangement 3000*a* opens. In this stressed condition, the diaphragm/flap valve arrangement 3000*a* will allow fluid to flow from the inlet 3010 to the outlet 3030. When the fluidic pressure in the inlet is removed, the diaphragm/flap 3040 will return to its initial position and seal the inlet 3010, preventing backflow.

Figure 15B:
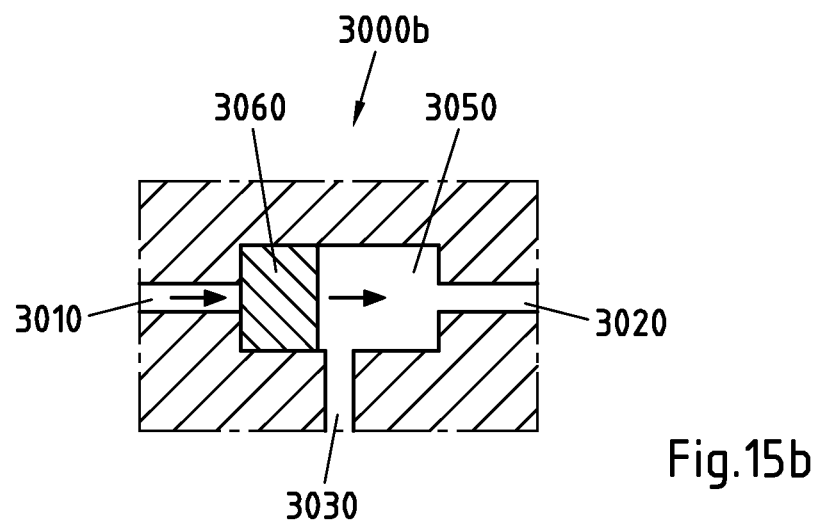

FIG. 15*b* illustrates a shuttling valve arrangement 3000*b*. The shuttling valve arrangement 3000*b* has a tube 3050. The tube 3050 has two inlets 3010, 3020 and an outlet 3030. In the tube 3050 a movable element 3060 (e.g a piston or a ball) is arranged.

The diameter of the movable element 3060 corresponds to the diameter of the tube 3050 such that the movable element 3060 is movable between a first and a second (longitudinal) position in the tube 3050. In the first position (illustrated in FIG. 15*b*), the movable element 3060 seals the inlet 3010 and allows fluid flow from the inlet 3020 to the outlet 3030. In the second position (not illustrated), the movable element 3060 seals the inlet 3020 and allows fluid flow from the inlet 3010 to the outlet 3030. When the fluidic pressure in the inlet 3010 is for instance increased (e.g. during a dose priming or a dose injecting step), the movable element 3060 will be pushed towards the second position as indicated by the arrow in FIG. 15*b*.

Figure 15C:
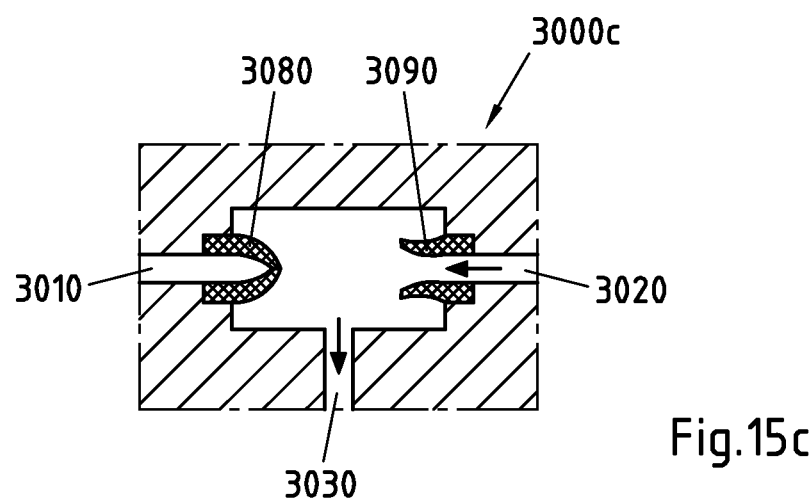

FIG. 15*c* illustrates a moulded duckbill valve arrangement 3000*c*. The moulded duckbill valve arrangement 3000*c* has a first and a second duckbill valve 3080, 3090. When the fluidic pressure in the inlet 3020 is increased (e.g. during a dose priming or a dose injecting step), the second duckbill valve 3090 will change from an un-stressed state to a stressed state. In the stressed state, the fluidic pressure inverts the naturally flattened shape of the duckbill valve as indicated in FIG. 15*c* so that the duckbill valve opens. In this stressed condition, the second duckbill valve 3090 will allow fluid to flow from the inlet 3020 to the outlet 3030. When the fluidic pressure in the inlet 3020 is removed, the second duckbill valve 3090 will return to its flattened shape and seal the inlet 3020, preventing backflow. The first duckbill valve 3080 operates in a similar manner as the second duckbill valve 3090 when the fluidic pressure is increased in the inlet 3010.

Figure 15D:
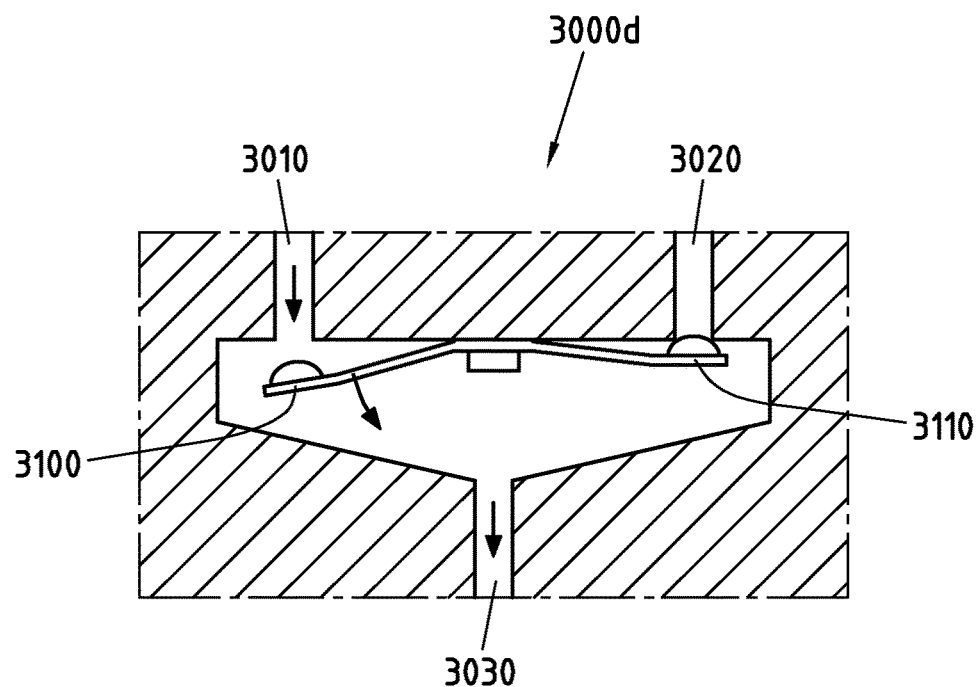

FIG. 15*d* illustrates a flat spring valve arrangement 3000*d*. The flat spring valve arrangement 3000*d* has a first and a second flat spring 3100, 3110. The first and the second flat spring 3100, 3110 may for instance be integrally formed.

When the fluidic pressure in the inlet 3010 is increased (e.g. during a dose priming or a dose injecting step), the first flat spring 3100 will change from an un-stressed state to a stressed state. In the stressed state, the fluidic pressure bends the first flat spring 3100 as indicated by the arrow in FIG. 15*d* so that the flat spring valve arrangement 3000*d* opens. In this stressed condition, the flat spring valve arrangement 3000*d* will allow fluid to flow from the inlet 3010 to the outlet 3030. When the fluidic pressure in the inlet is removed, the first flat spring 3100 will return to its initial position and seal the inlet 3010, preventing backflow. The second flat spring 3110 operates in a similar manner as the first flat spring 3100 when the fluidic pressure is increased in the inlet 3020.

Figure 15E:
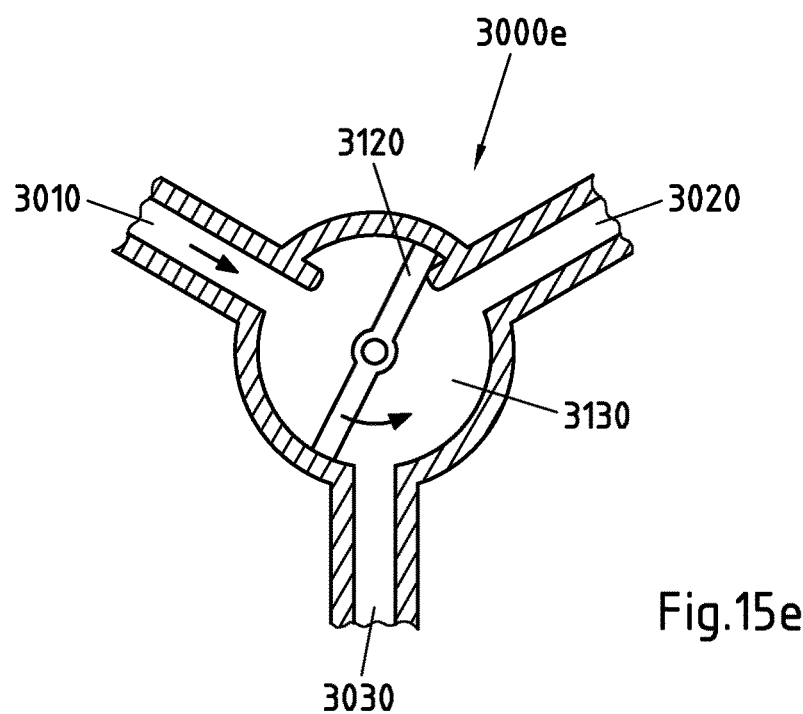

FIG. 15*e* illustrates a rotating flap valve arrangement 3000*e*. The rotating flap valve arrangement 3000*e* has a flap 3120 which is rotatably mounted in a valve chamber 3130. The valve chamber has two inlets 3010, 3020 and an outlet 3030.

The flap 3120 is rotatable between a first and a second position. In the first position (illustrated in FIG. 15*e*), the flap 3120 seals the inlet 3010 and allows fluid flow from the inlet 3020 to the outlet 3030. In the second position (not illustrated), the flap 3120 seals the inlet 3020 and allows fluid flow from the inlet 3010 to the outlet 3030.

When the fluidic pressure in the inlet 3010 is for instance increased (e.g. during a dose priming or a dose injecting step), the flap 3120 will be pushed towards the second position as indicated by the arrow in FIG. 15*e*.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2, des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the aforementioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A dispense interface for an ejection device, comprising:
    a first part comprising a substantially plate-like elongated shape,
    a second part comprising a substantially plate-like elongated shape,
    at least a first opening, a second opening, and a third opening,
    a fluidic channel, and
    a first connection element for the first opening, a second connection element for the second opening, and a third connection element for the third opening,
    wherein a top surface of said second part includes a substantially linear recess such that when said first part is joined to said second part, at least a part of said fluidic channel is formed connecting said first, second and third openings with each other,
    wherein the third connection element is configured to accept a needle assembly for a fluid tight connection with said third opening,
    wherein at least one of the first or the second connection elements is configured to provide a releasable push fit connection for a fluid tight connection with the ejection device,
    wherein the first, the second, and the third connection elements are produced from a plastic material and are an integral component with either the first part or second part, and
    wherein the fluidic channel is orientated in an elongate direction of the dispense interface such that the fluidic channel is substantially perpendicular to each of the first opening, the second opening, and the third opening.

2. The dispense interface according to claim 1, wherein at least one of said first part and said second part is produced by injection molding.

3. The dispense interface according to claim 1,
    wherein said first part comprises said third opening and said third connection element and wherein said second part comprises said first opening with said first connection element and said second opening with said second connection element.

4. The dispense interface according to claim 1,
    wherein said first opening is located at a first end of said second part and the second opening is located at a second end of said second part.

5. The dispense interface according to claim 4,
    wherein said third opening is located between said first end and said second end of said first part.

6. The dispense interface according to claim 1, wherein said third connection element is configured for a releasable connection with said needle assembly.

7. The dispense interface according to claim 1, wherein said fluidic channel comprises a substantially linear passage with a passage branching off for each opening.

8. The dispense interface according to claim 1, wherein at least one of said first, second, or third of the connection element is configured for at least one of a friction fit and a positive fit.

9. The dispense interface according to claim 1, wherein the needle assembly provides a male part of a Luer fitting.

10. The dispense interface according to claim 1, wherein said fluidic channel is configured such that a liquid can flow freely from any region of higher pressure to any region of lower pressure.

11. The dispense interface according to claim 1, wherein said fluidic channel comprises at least one non-return valve.

12. Method for preparing a dispense interface according to claim 1 comprising the steps of:
    attaching said dispense interface by means of said push fit connection to an ejection device having at least two reservoirs such that a fluid tight connection is established between said at least two reservoirs and said dispense interlace and attaching the needle assembly to said at least one connection element configured to accept the needle assembly of said dispense interface.

13. Method according to claim 12, further comprising the steps of ejecting a fluid from at least one of the reservoirs through the dispense interface and removing the dispense interface from the ejection device.

\* \* \* \* \*